(12) United States Patent
Lloyd et al.

(10) Patent No.: US 6,579,252 B2
(45) Date of Patent: Jun. 17, 2003

(54) SAFETY INDICIUM TO PROTECT BODY EXTREMITIES

(75) Inventors: Jeffrey Lloyd, 1941 Thayer Ave., Los Angeles, CA (US) 90025; Timothy Gordon, Scotch Plains, NJ (US)

(73) Assignee: Jeffrey Lloyd, Los Angeles, CA (US)

( * ) Notice: Subject to any disclaimer, the term of this patent is extended or adjusted under 35 U.S.C. 154(b) by 0 days.

(21) Appl. No.: 10/109,967

(22) Filed: Mar. 29, 2002

(65) Prior Publication Data

US 2002/0103452 A1 Aug. 1, 2002

Related U.S. Application Data

(63) Continuation-in-part of application No. 09/338,089, filed on Jun. 23, 1999.
(60) Provisional application No. 60/090,615, filed on Jun. 25, 1998.

(51) Int. Cl.[7] ................................................ A61F 13/00
(52) U.S. Cl. ............................ 602/60; 602/3; 602/61; 602/62; 602/63
(58) Field of Search ..................... 2/455–457; 604/289, 604/304, 308, 312; 602/1, 3, 5, 20, 23, 41, 60–63; 128/845–846, 856, 869

(56) References Cited

U.S. PATENT DOCUMENTS

| 4,947,867 A | * | 8/1990 | Keeton |
| 5,795,312 A | * | 8/1998 | Dye |
| 6,155,263 A | * | 12/2000 | Weaver |

* cited by examiner

*Primary Examiner*—Nicholas D. Lucchesi
*Assistant Examiner*—Lalita M. Hamilton
(74) *Attorney, Agent, or Firm*—Sitrick & Sitrick

(57) ABSTRACT

A method to and apparatus to prevent injury and infection of a health-care recipient as a result of anticipated possible complications associated with any ones of a predetermined plurality of health-care procedures. The invention provides specific unambiguous warning indications prohibiting one or more of the aforementioned procedures on the outer surface of a physical barrier which is placed onto said health-care recipient in such a way that the indications are clearly visible, or alternatively affixed as a decal to the skin of the patent. The presence of said barrier is designed to significantly interferes with any reasonable application said plurality of procedures on said recipient.

44 Claims, 14 Drawing Sheets

SAFETY INDICIUM TO PROTECT BODY EXTREMITIES

RELATED APPLICATIONS

This application is a continuation-in-part of the non-provisional application with Ser. No. 09/338,089, filed Jun. 23, 1999 and claiming the priority date from the provisional application with Ser. No. 60/090,615, filed Jun. 25, 1998.

FEDERALLY SPONSORED RESEARCH OR DEVELOPMENT

Not Applicable.

BACKGROUND OF THE INVENTION

This invention relates to the field of health care, and specifically to a system and methodology to warn and prevent health care providers from inadvertently causing injury or infection to same limbs and selected body parts, and to provide said warning by use of indicia for limbs and other selected body parts This invention relates to use in hospitals, acute care centers, emergency rooms, doctor's offices, nursing homes, convalescent hospitals, field hospitals and all other medical, nursing and health-care facilities, as well as out-patient or home care.

There are many situations where a body part or extremity must be protected from such a hospital procedure. For example, many women being treated for breast cancer have had the lymph nodes under their arms removed. As a result, because of the risk of developing lymphedema, the arm with no lymph nodes can never be used for intravenous cannula hook-ups, injections, or blood pressure readings.

At the present time, the most commonly used technique for alerting medical personnel to this condition is through the use of a temporary, handwritten note or sign which is typically taped on the wall over a patient's bed. This procedure is fraught with obvious failings: the sign may fall off the wall; it may not be seen; it may be ignored or lost in the clutter; it may be misunderstood or misinterpreted; it may contain incorrect information; and, it may not even be posted at all. Furthermore, a patient may be transported from one room to another, and the warning sign may be left behind.

SUMMARY OF THE INVENTION

It is an object of the present invention to provide instructive indications to protect a user's limb and other body part(s).

It is another object of the present invention to specifically prohibit particular health-care or medical procedures provided to the user by warning a health-care provider.

It is another object of the present invention to prevent injury to the user's body parts marked by the present invention by warning applied to same for medical or health-care procedures.

It is another object of the present invention to force a health-care provider or medical person to explicitly and pro-actively remove and/or disregard the indicium in order to circumvent the warning afforded by the present invention in use.

It is another object of the present invention to permit detection of the circumvention of the present invention in use.

In an alternate embodiment, it is an object of the present invention to specifically cover and protect a user's limb and other body part(s), and to prevent and make very difficult particular predefined medical or health-care procedures from being performed on the user's covered and protected body parts.

These and other aspects and attributes of the present invention will be discussed with reference to the following drawings and accompanying specification.

BRIEF DESCRIPTION OF THE DRAWINGS:

FIGS. 1–13 illustrate warning decals and warning indicia embodiments of the present invention, wherein:

FIG. 7 is an illustration of embodiments of the present invention as used on a person.

FIG. 8 is an illustration of safety cover and directly applied to the skin embodiments of the present invention as used on a person's arm.

FIG. 9 is an illustration of embodiments of the present invention as used on a person's arm and a safety cover used on a person's upper chest.

FIG. 10 is an illustration of safety cover and directly applied to the skin embodiments of the present invention as used on a person's feet.

FIG. 11 is an illustration of safety cover and directly applied to the skin embodiments of the present invention as used on a person's ear.

FIG. 12 is an illustration of safety cover and directly applied to the skin embodiments of the present invention as used on a person's arm and shoulder.

FIG. 13 is an illustration of safety cover and directly applied to the skin embodiments of the present invention as used on a person's leg.

Figure 1A:
FIG. 1A is an illustration of a blood pressure warning graphic and text associated with one embodiment of the present invention.

DETAILED DESCRIPTION OF THE PREFERRED EMBODIMENT:

While this invention is susceptible of embodiment in many different forms, there is shown in the drawings, and will be described herein in detail, specific embodiments thereof with the understanding that the present disclosure is to be considered as an exemplification of the principles of the invention and is not intended to limit the invention to the specific disclosed embodiments.

The present invention provides an indicium as a visible warning to prevent access to a particular part of a patient, so as to inhibit access to the particular part of the patient to provide a prohibition of a medical health care procedure as well as to precisely identify the exact location for a particular medical treatment. Various embodiments of the warning indicia include use(s) of temporary dies, inks, powders, adhesive decals and any other means to directly affix the instructive indications to the user's epidermis.

In accordance with a first embodiment of the present invention, a warning indicium is designed to protect an arm, hand, leg, foot, or any other body part or collection of body parts from a needle injection, intravenous hook-up, blood pressure reading, temperature measurement, or another similar medical procedure. (See FIGS. 1–13.)

The warning indicium embodiment of the present invention, once applied to the patient, provides and acts as a visual prohibition of a medical health care procedure and as a precise locator for a medical procedures. Through the use of bright colors and descriptive graphics (similar to the familiar "no smoking symbol") emblazoned upon it, the present invention alerts any medical staff member that the marked body part is not to be used for any medical procedure. In an alternate embodiment, the warning indicium provides a graphic bull's-eye that identifies the precise location where a procedure is to take place.

Some of the more common medical procedures are identified in FIGS. 1A–1C and FIGS. 2A–2F illustrate alternate embodiments of warning indications for various graphics alerting medical staff that taking a blood pressure reading, and/or using a blood pressure cuff, on the relevant users' body part(s) is prohibited. The graphical warning may be supplemented by a textual description or prohibition. Additionally, the textual warning may be supplied in more than one language.

FIGS. 1A–1C and FIGS. 2A–2F illustrate alternate embodiments of warning indicia including graphics and text.

Figure 2A:
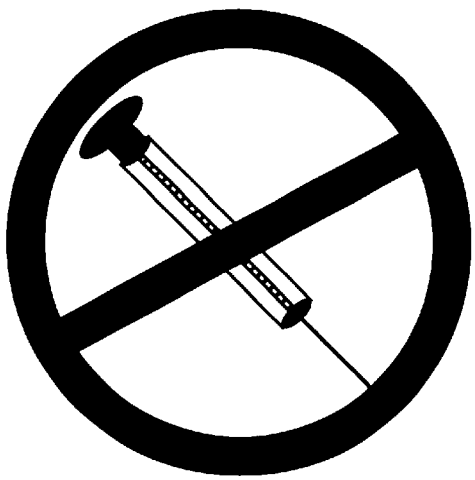
FIG. 2A is an illustration of a hypodermic warning graphic associated with an embodiment of the present invention.
Figure 2B:
FIG. 2B is an illustration of a blood pressure warning graphic associated with an embodiment of the present invention.

FIGS. 1A and 2B illustrate alternate embodiments of warning indication graphics, as placed on the patient's body, alerting medical staff that applying an apparatus to measure blood pressure on the relevant users' body part(s) is prohibited. The graphical warning may be also be supplemented by or replaced with a textual description or prohibition. As before, the textual warning may be supplied in more than one language.

Figure 1B:
FIG. 1B is an illustration of an injection warning graphic and text associated with one embodiment of the present invention.

FIGS. 1B and 2A illustrate alternate embodiments of warning indication graphics, as placed on the patient's body, alerting medical staff that injecting material, and/or using a hypodermic needle, on the relevant users' body part(s) is prohibited. The graphical warning may be also be supplemented by or replaced with a textual description or prohibition. As before, the textual warning may be supplied in more than one language.

Figure 1C:
FIG. 1C is an illustration of an intravenous warning graphic and text associated with one embodiment of the present invention.
Figure 2C:
FIG. 2C is an illustration of an intravenous warning graphic associated with one embodiment of the present invention.

FIGS. 1C and 2C illustrate alternate embodiments of warning indication graphics alerting medical staff that drawing material, or using a cannula, on the relevant users' body part(s) is prohibited. The graphical warning may be also be supplemented by a textual description or prohibition. As before, the textual warning may be supplied in more than one language.

Figure 2D:
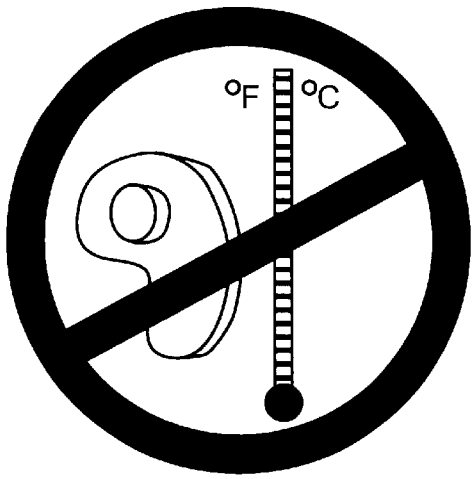
FIG. 2D is an illustration of a temperature warning graphic associated with an embodiment of the present invention.

FIG. 2D illustrates an embodiment of a warning indication graphic alerting medical staff that taking or monitoring a temperature of the relevant body part is prohibited.

Figure 2E:
FIG. 2E is an illustration of a moisture warning graphic associated with an embodiment of the present invention.

FIG. 2E illustrates an embodiment of a warning indication graphic alerting medical staff that moisture on of the relevant body part is prohibited.

Figure 2F:
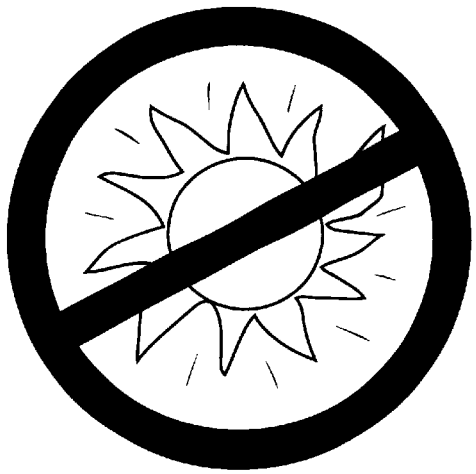
FIG. 2F is an illustration of a bright-light warning graphic associated with an embodiment of the present invention.

FIG. 2F illustrates an embodiment of a warning indication graphic alerting medical staff that bright light is to be avoided.

FIG. 2D illustrates an embodiment of a warning indication graphic alerting medical staff that taking or monitoring a temperature of the relevant body part is prohibited.

FIG. 2E illustrates an embodiment of a warning indication graphic alerting medical staff that moisture on of the relevant body part is prohibited.

FIG. 2F illustrates s an embodiment of a warning indication graphic alerting medical staff that bright light is to be avoided.

The actual graphic images used in accordance with the invention are not limited to the examples shown. Additionally, images (preferably that have been tested to be readily discernable by the medical profession) can supplement or replace the examples shown herein. Any image may be supplemented or replaced by textual warnings, and the warnings may appear in any number of languages.

In an alternate embodiment of the invention, the textual warnings stand-alone and are used in lieu of graphic images.

The warning indication graphic images can be one or more of graphics, icons, pictographs, and other visual, audible, or other method or means used to convey information regarding prohibited medical procedures to medical staff.

In accordance with an alternate embodiment, the warning indicium or indicia is/are placed onto a sheath that is placed over the body part. (See FIGS. 3–13.)

The cover embodiment of the present invention provides a barrier, both physically and with a warning (visual, audible, etc.) to prevent access to a particular part of a patient, so as to inhibit access to the particular part of the patient to provide a barrier to a medical health care procedure. Various embodiments of the cover barrier include sleeves (arms, legs, etc.), vests (shoulder, chest, etc.), pockets (hands, feet, ankles, etc.), covers (ears, nose, face), screens, wraps, and others.

In accordance with a first cover embodiment of the present invention, a sleeve is designed to shield, cover or protect an arm, hand, leg, foot, or any other body part or collection of body parts from a needle injection, intravenous hook-up, blood pressure reading, temperature measurement, or another similar medical procedure. (See FIGS. 3–13.)

The safety cover sleeve embodiment of the present invention, once applied to the patient as a barrier to a medical health care procedure, eliminates the problems associated with the prior art methods. Through the use of bright colors and descriptive graphics (similar to the familiar "no smoking symbol") emblazoned upon it, the present invention would automatically alert any medical staff member that the covered body part is not to be used for any such medical procedure.

Figure 3A:
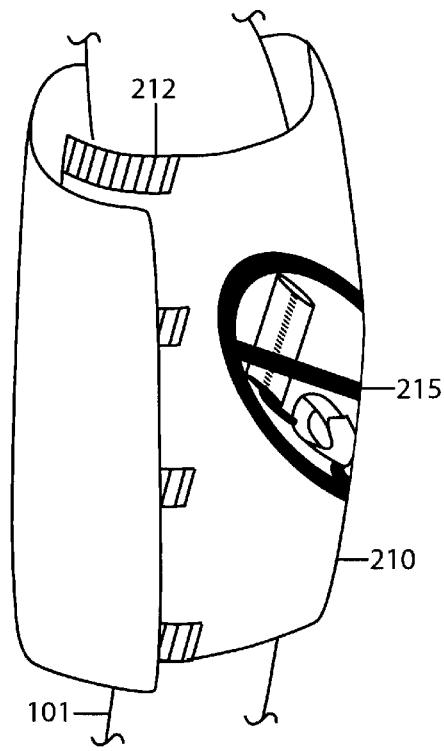
FIG. 3A is an illustration of one safety cover embodiment of the present invention as applied to a person's arm.
Figure 3B:
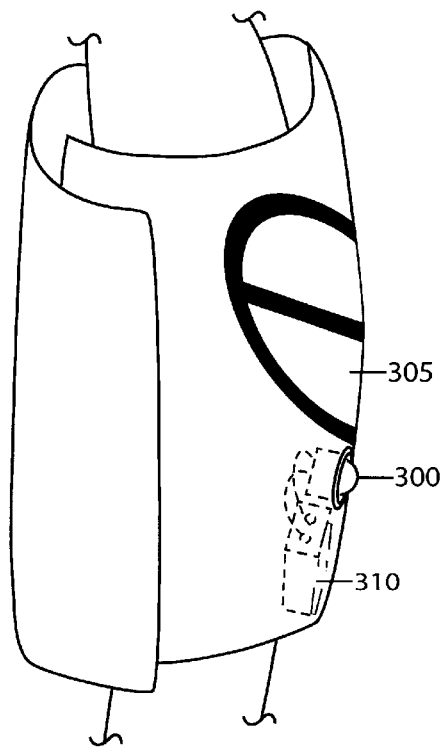
FIG. 3B is an illustration of an alternate safety cover embodiment of the present invention including a battery-operated warning light.

In an alternate cover embodiment as shown in FIG. 3B, an indicator 300 is incorporated that lights up to draw attention to the warning 305. One of the simplest embodiments is the use of a small battery operated flashing light-emitting diode (LED); such a device could run for weeks on a single battery 310. Other embodiments may include incandescent bulbs, neon or other rare-gas bulbs, and others familiar to one skilled in the arts.

An alternate cover embodiment features glow-in-the-dark material on the warning, such that the warning would be visible in darkness or near darkness.

In all cover embodiments, the warning may be affixed to, woven into, painted or printed on, or otherwise made part of or visible from at least one surface of the cover safety sleeve or other barrier in accordance with the present invention. The key attribute of the warning is that it should provide a specific unambiguous warning indication, to clearly indicate to a health-care provider or medical staff, that specific medical procedures are to be prohibited on the protected body part.

In a preferred cover embodiment, more than one warning may be visible on the cover safety sleeve or other barrier embodiment. In this embodiment, each warning is a clear indication of a specific medical procedure that is prohibited for the protected body part. As a result, this cover embodiment of the invention simultaneously prohibits a plurality of different medical procedures.

In use, multiple instances of the safety cover, sleeve or other barrier embodiment may be used on one patient simultaneously, generally on different body parts. It is also possible to use multiple cover safety sleeves on one specific body part.

The cover barrier can be made out of inexpensive, disposable material that is durable enough to remain in place without easily tearing, but flexible enough not to cause any discomfort or pain. Materials suitable for construction of the cover of the present invention include paper, cotton, cloth, gauze, silk, plastic, latex, rubber, polyester and other similar materials. The materials can alternatively be chosen for reusability, as durable and washable materials.

In a preferred cover embodiment, the materials selected for construction would permit easy sterilization of the cover invention prior to use.

Figure 4A:
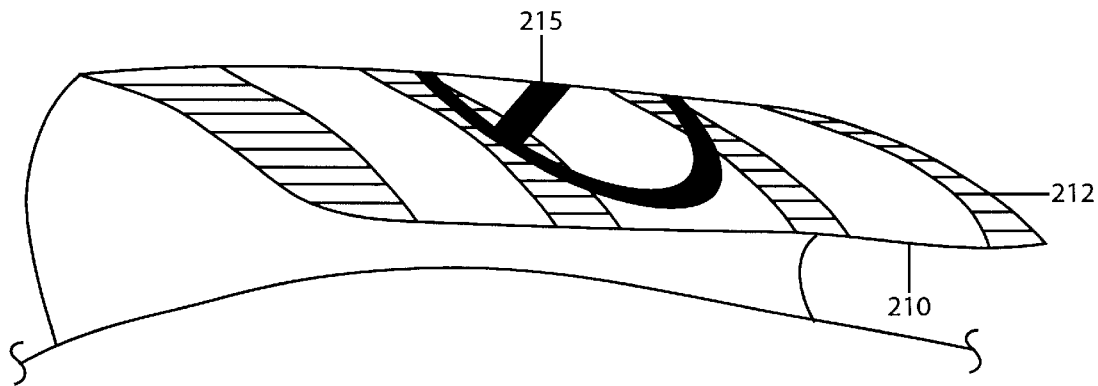
FIG. 4A is an illustration of one safety cover embodiment of the present invention in the process of being applied to a person's arm.
Figure 4A:
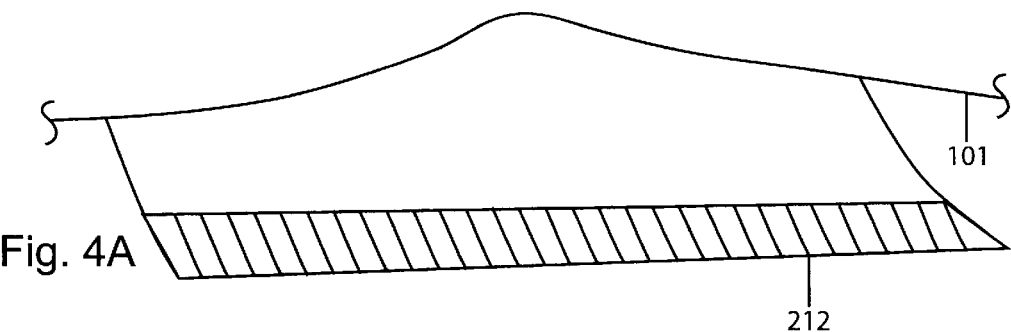
Figure 5A:
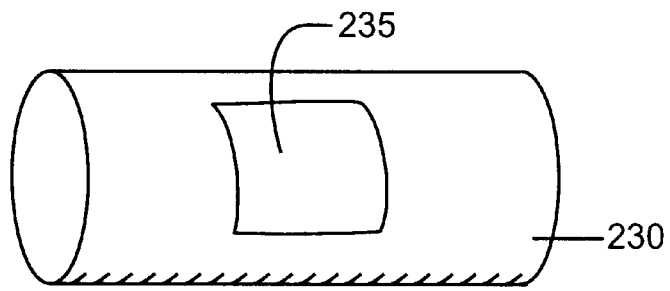
FIG. 5A is an illustration of an alternate safety cover embodiment of the present invention as a single-ended cylindrical pocket.
Figure 5B:
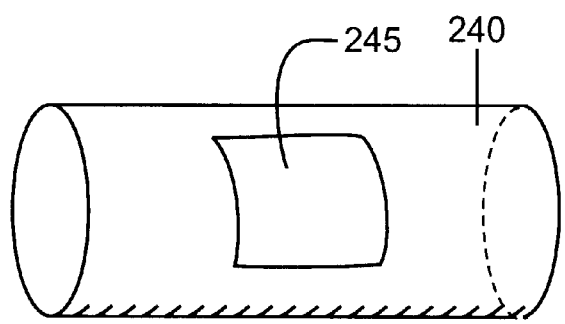
FIG. 5B is an illustration of an alternate safety cover embodiment of the present invention as a double-ended cylindrical sleeve.

FIGS. 3A and 4A illustrate one seam in the safety sleeve 210. In a preferred cover embodiment, no seam is present, and the safety sleeve represents a continuous unbroken cylinder as shown in FIGS. 5A and 5B. In another cover embodiment, the safety sleeve may have a plurality of seams, each with their own respective fastening means.

FIGS. 3A, 3B, 4A, 4B, 5A–5C and 6A–6D show various cover embodiments of the present invention including the warning present on the outer surface of the safety sleeve. FIG. 3A illustrates the barrier wrap 210 of FIG. 4A, having completed the process of being applied to a person's arm and being in the closed position or configuration. The safety barrier wrap sleeve 210 is shown in the closed configuration, with the arm 101 encircled by the safety sleeve.

FIG. 4A is an illustration of a one cover embodiment of a barrier wrap 210 having warning indication 215 in accordance with the present invention in the process of being applied to a person's arm 101. The safety sleeve is shown in the open configuration with fastener means 212 shown, with the arm 101 placed into the center of the sleeve, before the safety sleeve is closed around the patient's arm.

FIG. 5A is an illustration of one cover embodiment of a single-ended cylindrical pocket barrier 230 with warning indication 235, suitable for use on a patient's limb or other extremity.

FIG. 5B illustrates one cover embodiment of a double-ended cylindrical sleeve barrier 240 with warning indication 245, suitable for use on an elbow, wrist, knee, or ankle joint. A larger version of the cover embodiment shown in FIG. 5B is suitable for use on a torso.

Figure 5C:
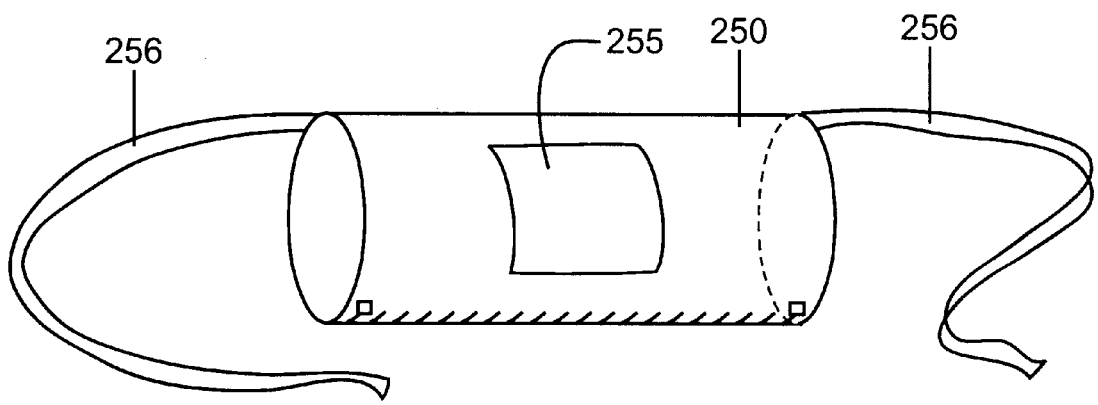
FIG. 5C is an illustration of another safety cover embodiment of the present invention as a double-ended cylindrical sleeve including tie straps.

FIG. 5C is an illustration of another cover embodiment of a double-ended cylindrical sleeve barrier 250 having warning indication 255 including tie straps 256 to assist the positioning and placement of the safety sleeve 250.

Figure 6A:
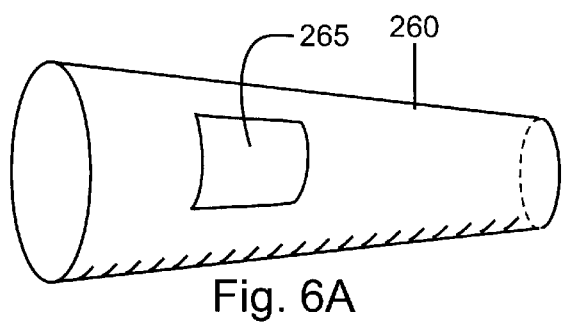
FIG. 6A is an illustration of another alternate safety cover embodiment of the present invention as a double-ended conical sleeve.

FIG. 6A is an illustration of one cover embodiment of a double-ended conical sleeve barrier 260 with warning indication 265. This shape is more suitable for some patients to protect lower extremities such as a complete leg.

Figure 6B:
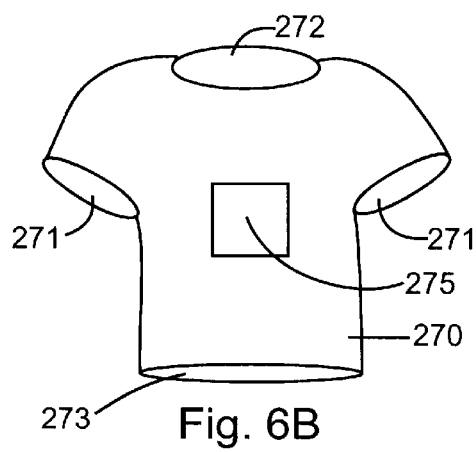
FIG. 6B is an illustration of a shirt safety cover embodiment of the present invention illustrated in the form of a shirt.

FIG. 6B is an illustration of a cover embodiment of a shirt barrier 270 having warning indication 275, and comprising holes for arms 271, neck 272, and torso 273.

Figure 6C:
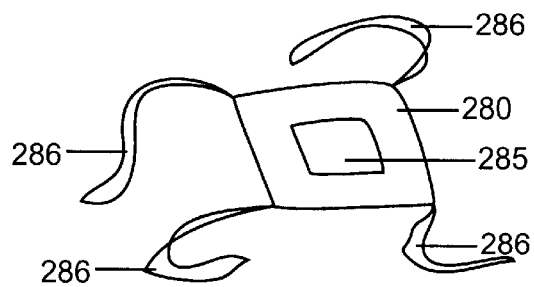
FIG. 6C is an illustration of a patch safety cover embodiment of the present invention as a warning patch with tie straps.

FIG. 6C is an illustration of an alternate cover embodiment of a warning patch barrier 280 with warning indication 285 with tie straps 286. This embodiment is suitable for very small areas that need protection that would be otherwise difficult to encompass by the other embodiments.

Figure 6D:
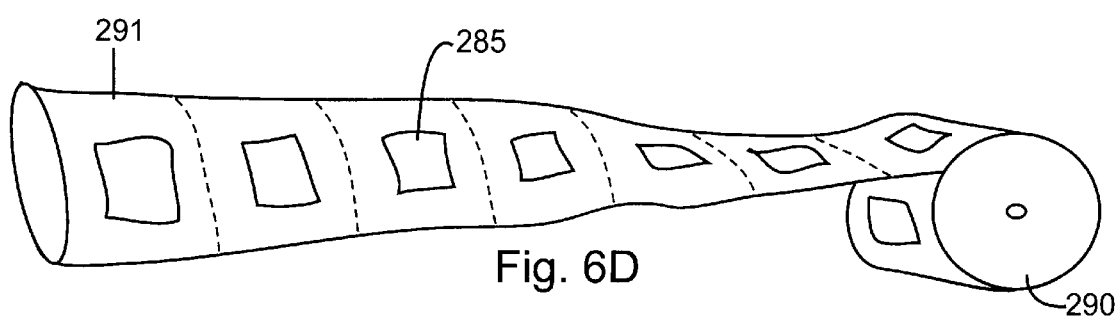
FIG. 6D is an illustration of a safety cover embodiment of the present invention wherein, for example, the safety covers of FIGS. 5A–C are supplied as a continuous roll.

FIG. 6D is an illustration of one cover embodiment of the present invention wherein the barrier is initially supplied as a continuous roll 290. A number of segments 291 of safety sleeve with warning indication 285 are constructed with perforations separating each segment from the next, and the segments are rolled for distribution. In use, the user would select the number of segments required and tear off that length from the roll, thus reducing waste.

The sleeve would remain in position on a patient through the use of any of the following devices, including self-adhesive strips, hook and loop fasteners, buttons, zippers, hooks and eyes, ties, buckles, belts, pins, string, elastic bands, rubber bands, snaps, clasps, tape fasteners, or any other clasping, fastening, or adhesive device.

The fasteners may be used to fasten solely to other portions of the safety sleeve. In a preferred embodiment, the fasteners may alternatively fasten to elements of the patient's existing clothing, thus permitting additional ease of installation and use of the invention. In an alternate embodiment, the invention may be fastened directly to the patient's skin, using suitable adhesives well-known to those in the medical profession.

In a preferred cover embodiment, the invention includes a means to detect if the cover has been removed and/or opened at any time during its use. This detection means may utilize any of fragile tape, single-use stickers, color-change chemicals, phase-change chemicals, a mechanical indicator, limit switches, or a position sensor. If the invention has been opened or removed at any time, the detection means provides obvious and unchangeable evidence of such tampering. In one preferred cover embodiment, the detection means provides an alarm trigger output, which can be used to alert medical or nursing staff at a monitoring station or within some signaling range that the invention has been tampered with.

In addition to tampering and removal, one cover embodiment of the present invention permits detection of unusual attributes such as elevated or depressed temperature, high or low pH values, presence or absence of moisture, and so on. Additionally, in another cover embodiment, motion inside the safety sleeve can be detected. A different cover embodiment of the invention permits sensing of blood oxygenation level. Each of these attributes may be used to trigger an alarm or as a data input to an external medical system.

In an advanced cover embodiment, the safety sleeve includes motion and/or proximity sensors, using any conventional sensing means known to those skilled in the arts, including active and passive infrared (IR), ultrasonic, trembler, and vibration sensors. These sensors may trigger an alarm within some signaling range indicating attempted access or tampering with the safety sleeve by someone external to the patient.

In a preferred cover embodiment, the material of the safety sleeve is flexible, lightweight, inexpensive, sterile, and disposable. In one embodiment, the safety sleeve may be one of water-resistant, water-proof, or water-tight. In another cover embodiment, the safety sleeve may be gas-tight permitting air pressurization or vacuum.

Figure 4B:
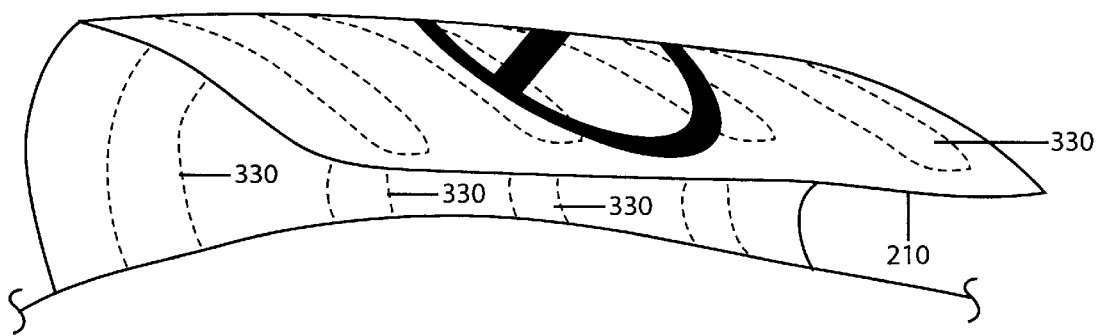
FIG. 4B is an illustration of another safety cover embodiment of the present invention which incorporates a support structure and an alternate fastening means.
Figure 4B:
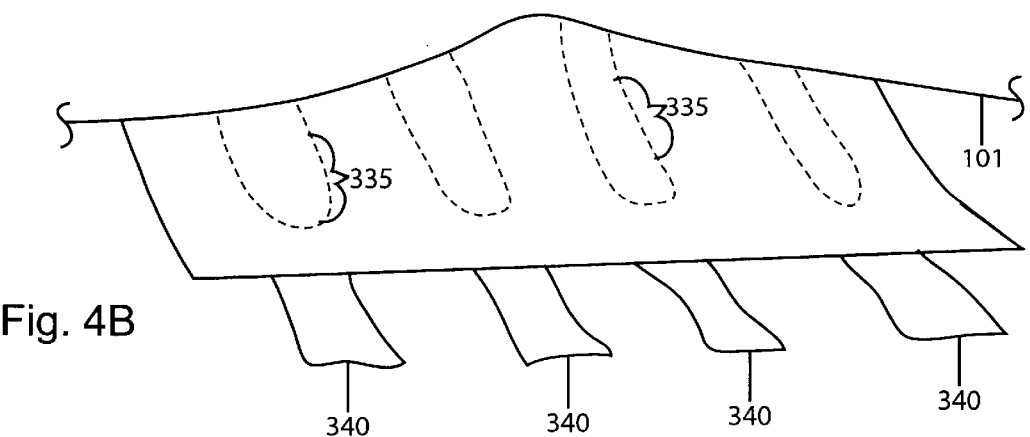

In one cover embodiment, as shown in FIG. 4B, the safety sleeve incorporates internal support structures to permit the sleeve to maintain a shape or profile independently of the patient's body part. These supports may include ribs, rings, stays, splints, restraints, air cushions, water cushions, aerogels, braces, and/or supports. As shown in FIG. 4B, support ribs 330 may be affixed to the safely sleeve barrier wrap 210 by means of stitches 335 or other attachment means. Alternatively, the support ribs may be formed as an integral part of the safety sleeve barrier wrap 210. In the illustrated cover embodiment, self-adhesive tabs 340 are shown to fasten the safety sleeve in place.

Some of the more common medical procedures are identified in FIGS. 1A–2F illustrate alternate embodiments of warning indications for various graphics alerting medical staff that taking a blood pressure reading, and/or using a blood pressure cuff, on the relevant users' body part(s) is prohibited. The graphical warning may be supplemented by a textual description or prohibition. Additionally, the textual warning may be supplied in more than one language.

Figure 7:
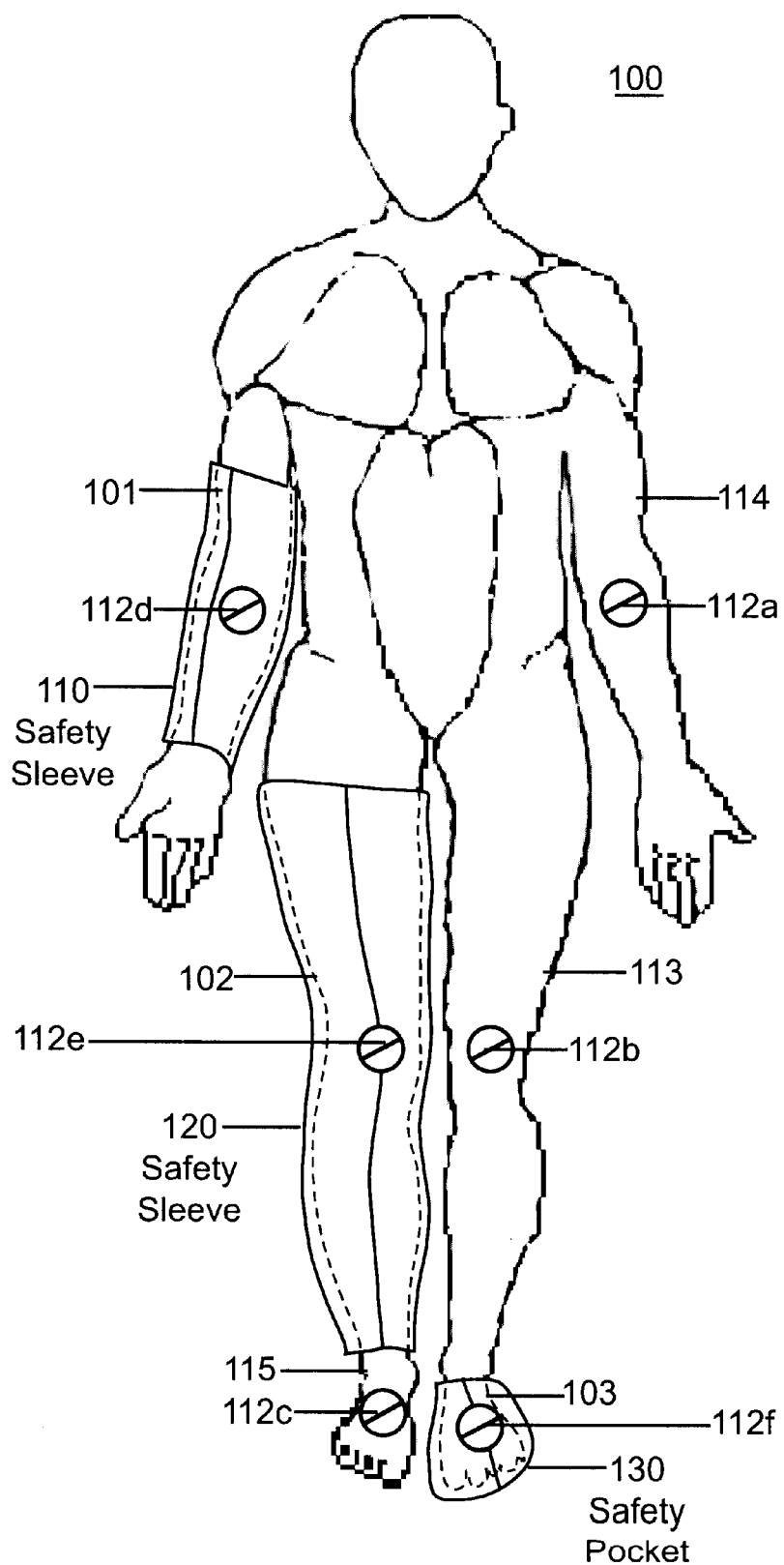

FIG. 7 is an illustration of various warning indicia and cover embodiments of the present invention as used on a person. Six warning indicia are shown; one warning indicium 112a is present applied directly to the epidermis on one arm 114 of a person 100; one warning indicium 112b is present applied directly to the epidermis on one leg 113 of a person 100; one warning indicium 112c is present applied directly to the epidermis on one foot 115 of a person 100; one warning indicium 112d is present on one safety sleeve barrier 110 on one arm 101 of a person 100; one warning indicium 112e is present on one barrier 120 on one leg 102 of a person 100 and one warning indicium 112f is present on one safety pocket 130 on one foot 103 of a person 100.

Figure 8:
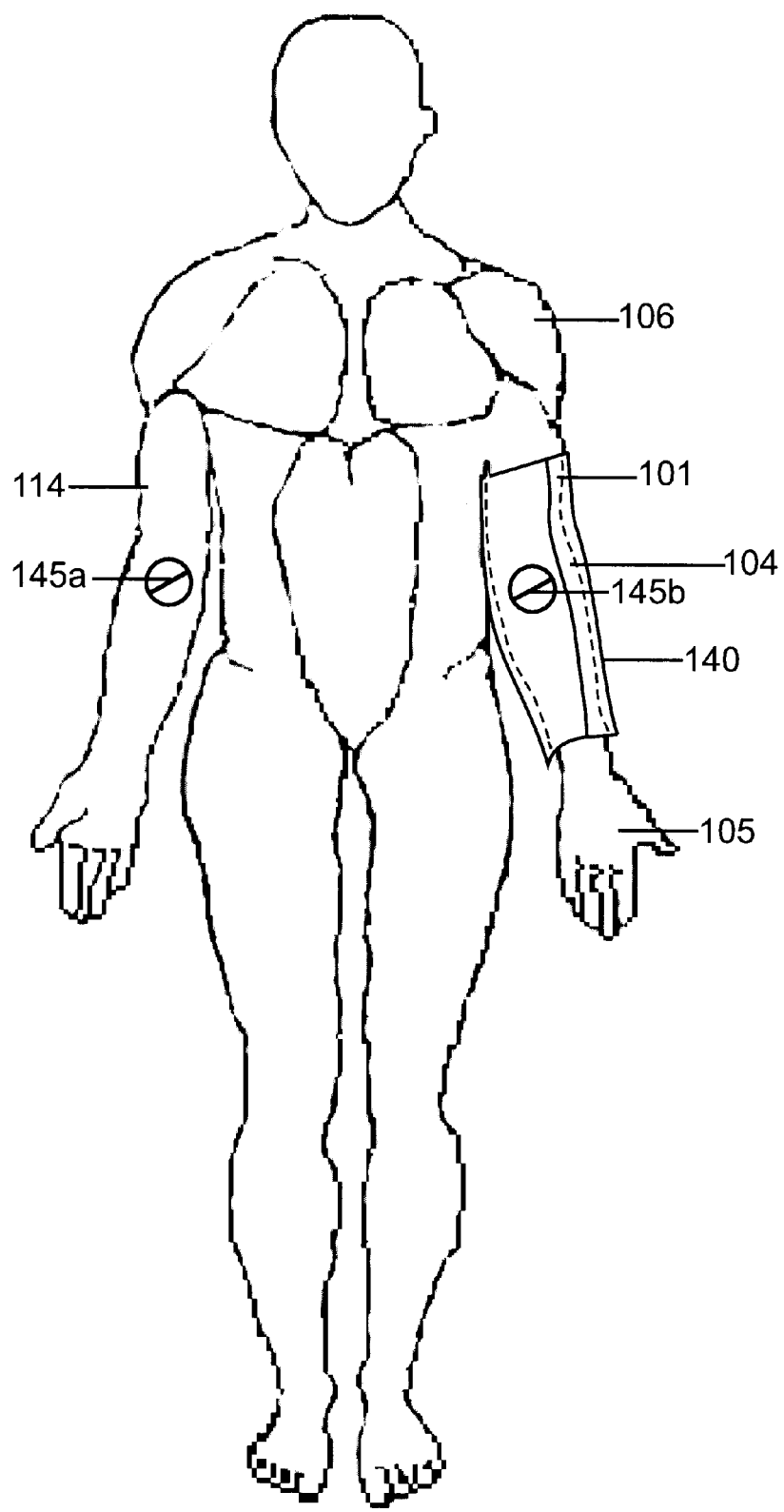

FIG. 8 is an illustration of two warning indicia embodiments wherein the warning indication 145a is used on the epidermis of the arm 114 excluding all areas not covered by the indicium and on a cover barrier sleeve 140 with warning indication 145b as used on a person's arm 101 including an elbow 104 but excluding both the hand 105 and shoulder 106.

Figure 9:
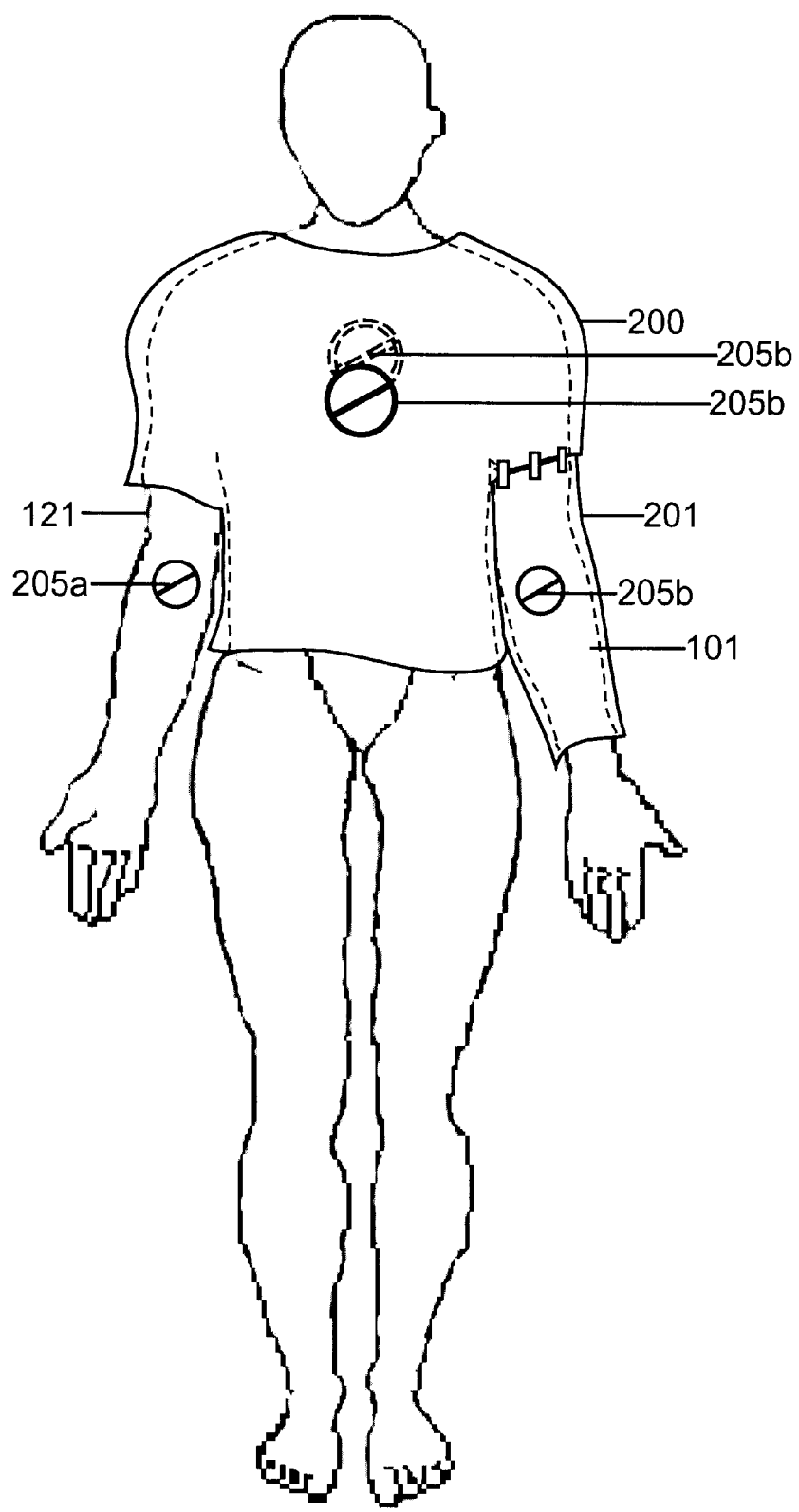

FIG. 9 is an illustration of a four warning indicia embodiments wherein the warning indication 205a is used on the epidermis of the arm 121, the upper chest 111 excluding all areas not covered by the indicium and on the cover barrier 200, 201 having warning indication 205b in accordance with the present invention as used on a person's arm 101 and upper chest 111. This illustration shows two safety sleeves 200, 201 of differing design connected via fasteners to form a continuous safety covering.

Figure 10:
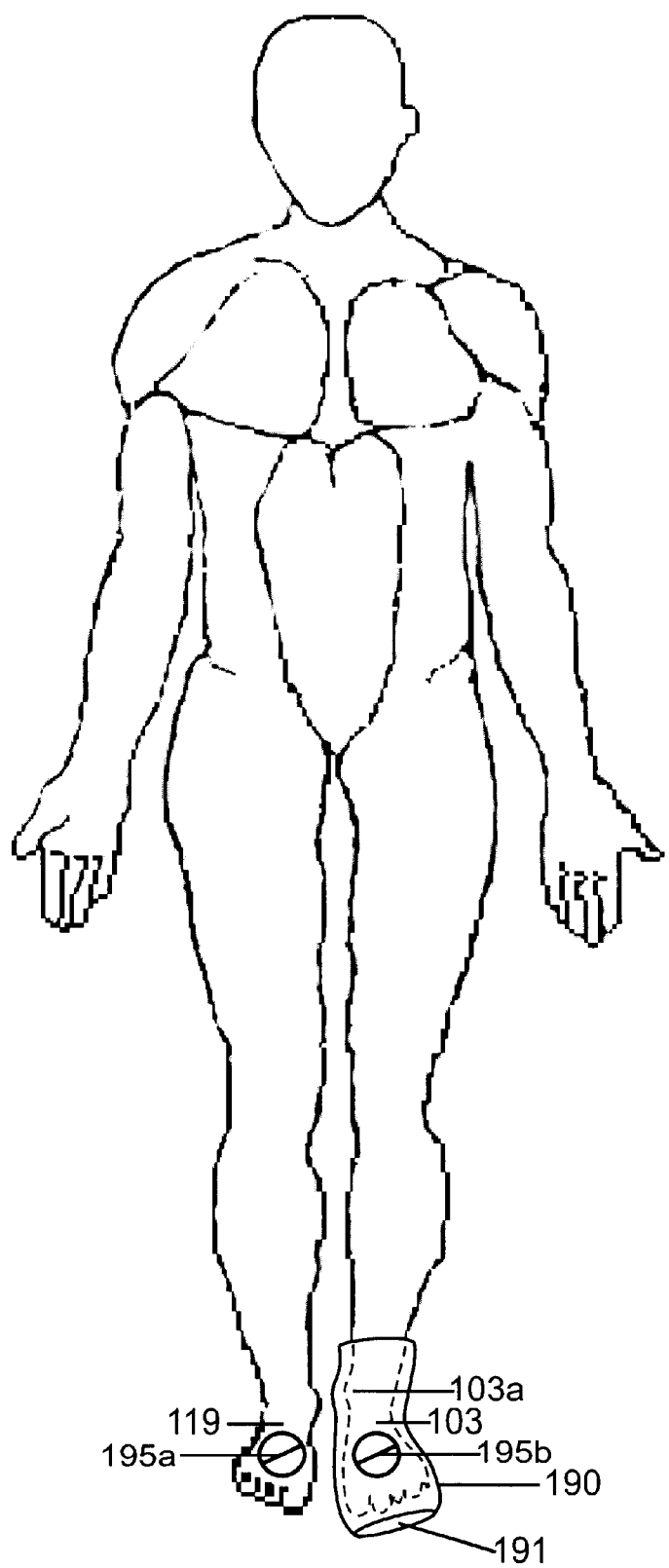

FIG. 10 is an illustration of a two warning indicia embodiments wherein the warning indication 195a is used on the epidermis of the foot 119 excluding all areas not covered by the indicium and on a cover barrier 190 having warning indication 195b in accordance with the present invention as used on a person's foot 103. FIG. 10 shows the use of one pocket 190, on foot 103, wherein the safety sleeve 190 is open on the bottom end 191. The foot 103 is thus protected from the ankle 103a on down to the bottom end 191.

Figure 11:
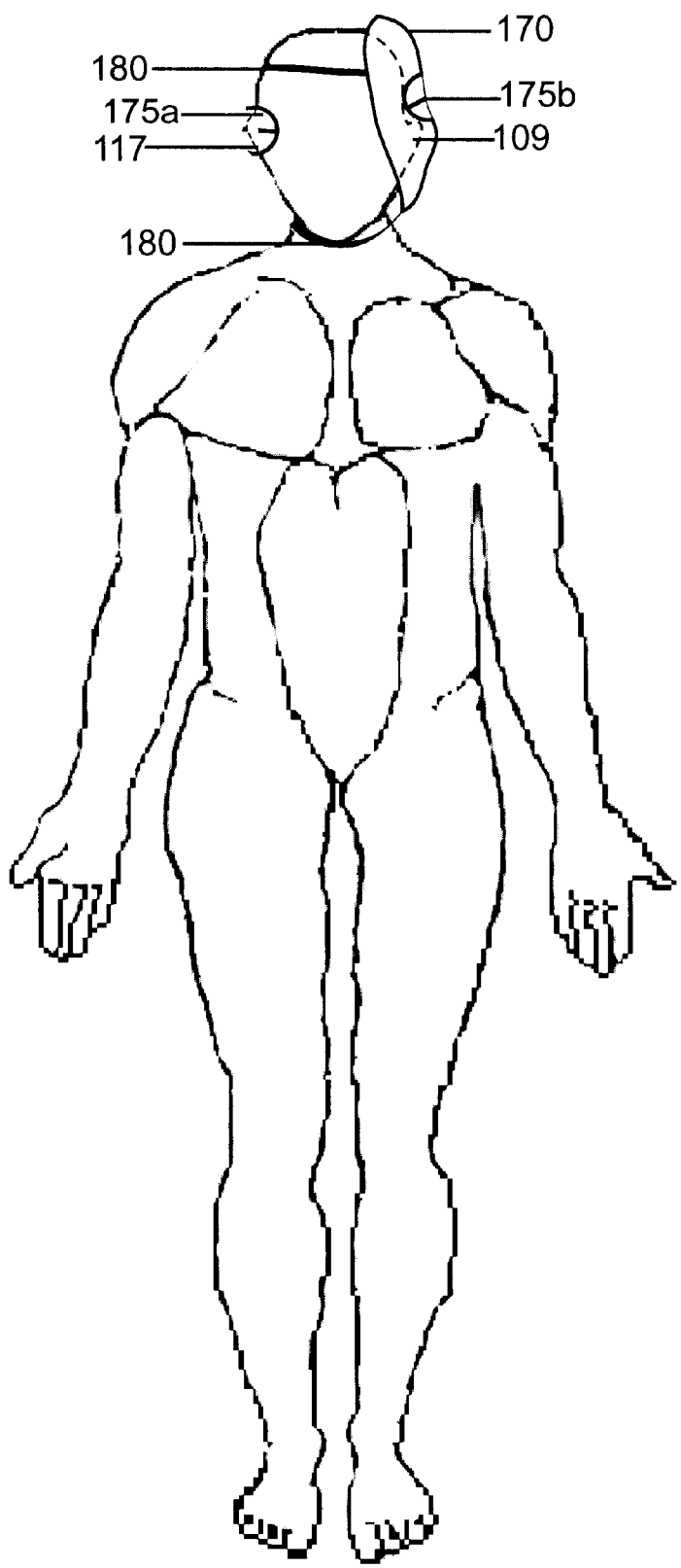

FIG. 11 is an illustration of a warning indicium embodiment 175a used on the epidermis of the ear 117 excluding all areas not covered by the indicium and on a cover barrier 170 having warning indication 175b in accordance with the present invention as used on a person's ear 109. This cover embodiment also illustrates the use of straps or belts 180 to hold the surface of the protective safety cover 170 in place. In a preferred embodiment, the straps 180 are constructed of a stretchable and breathable fabric such as an elastic weave.

Figure 12:
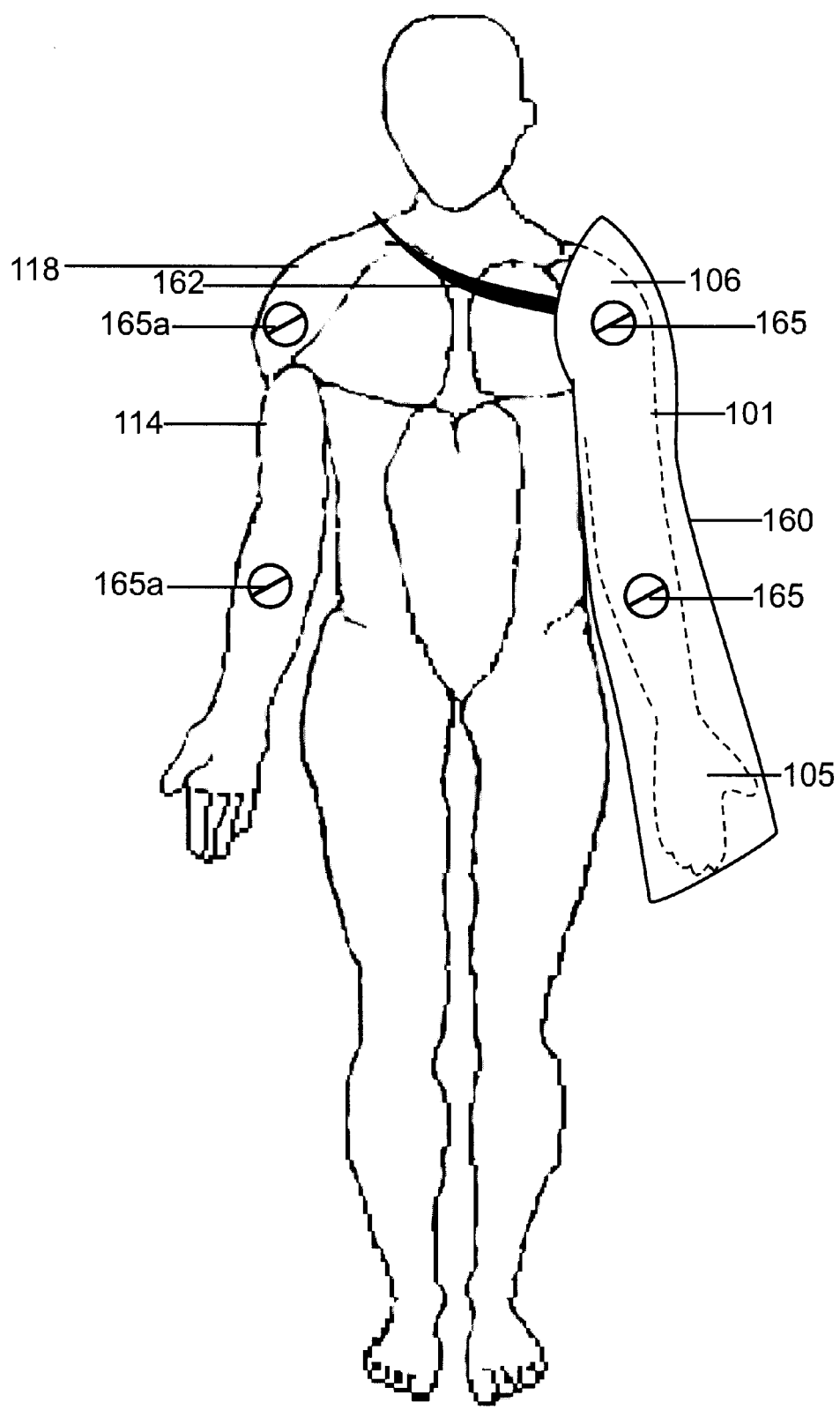

FIG. 12 is an illustration of four warning indicia embodiments wherein the indication 165a is used on the epidermis of the arm 114 and shoulder 118 excluding all areas not covered by the indicia and on a cover barrier 160 having a warning indication graphic 165b in accordance with the present invention as used on a person's arm 101 and shoulder 106. This embodiment also illustrates the use of a strap 162 or belt to hold the upper portion of the sleeve in place. The illustrated embodiment has an opening at the bottom end permitting access to the patient's hand 105. In an alternate of this cover embodiment, the bottom may be sealed thus preventing access to the patient's hand.

Figure 13:
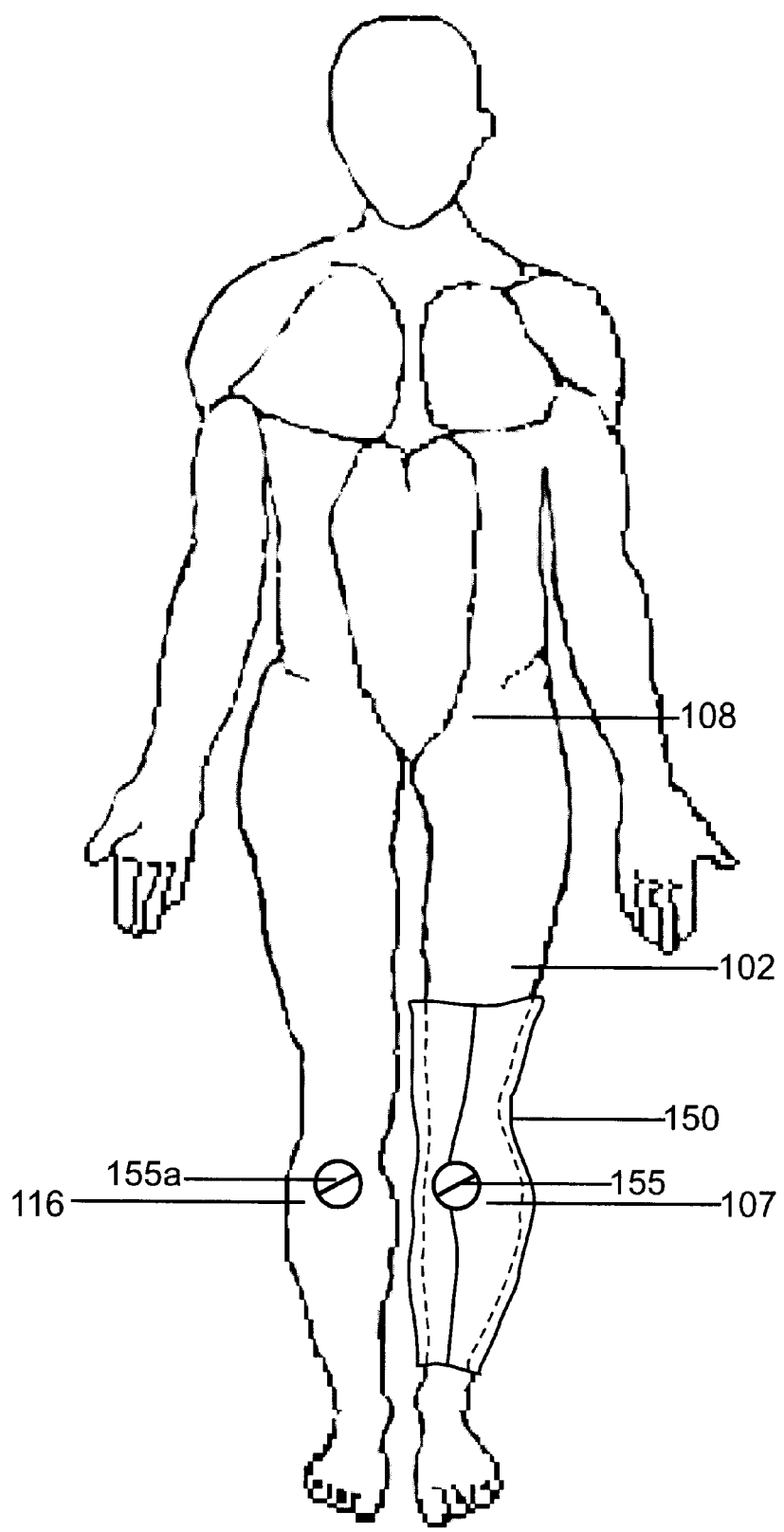

FIG. 13 is an illustration of two warning indicia embodiments wherein the indication 155a is used on the epidermis of the knee 116 excluding all areas not covered by the indicium and on a barrier sleeve 150 with warning indication 155b on a viewable surface as used on a person's leg 102, including the knee 107 and excluding the pelvis 108 and foot 103.

Figure 14:
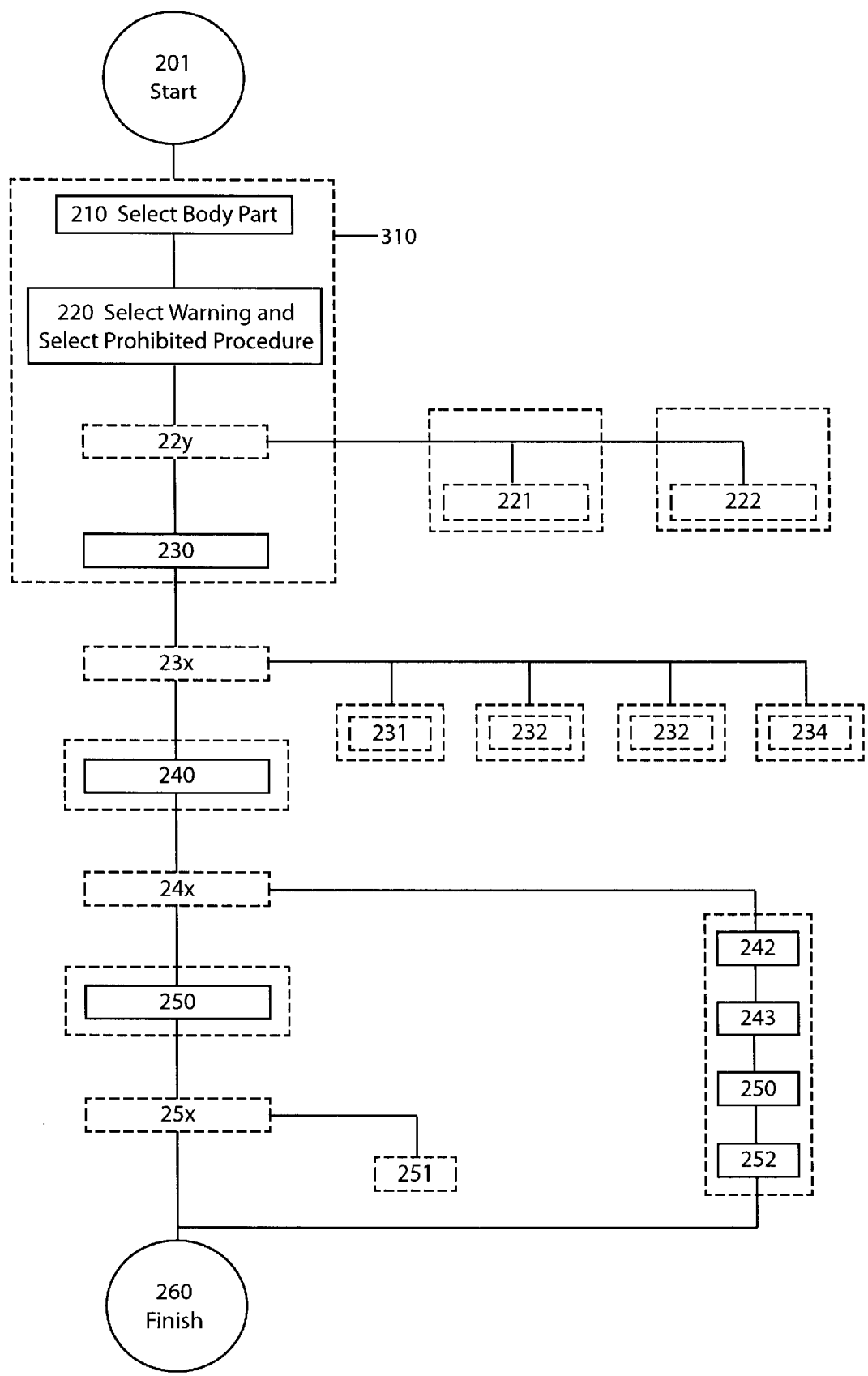
FIG. 14 illustrates the process steps in the methodology of the present invention in flow-chart form.

FIG. 14 illustrates the process flow and steps and the methodology to provide a selected warning indicium to preclude a selected prohibited physical treatment of a selected body part of a patient (210, 220). Alternately, a plurality of separate warnings for respective prohibited physical treatments can be selected (221). The method further comprises providing a visual warning on an indicium against a specific prohibited physical treatment (230); placing the indicium over a body part of the patient to inhibit access to the prohibited physical treatment (240); and positioning and placing the indicium over the body part in such a way that subsequent to the placing, the warning on the indicium is visible and displays the warning to any person attempting the prohibited access of the body part. The warning can be generic to a treatment or can be specific to a medical condition, and alerts against the prohibited physical treatment. In one embodiment, the warning additionally comprises at least one of a graphic image, a color warning, an icon warning and a textual warning (231).

Alternatively, the method further comprises providing a plurality of separate warnings on said indicium (232). In one embodiment, the step of placing further comprises the method of attaching said indicium to cover a portion of clothing on said patient (233). Alternatively, or additionally, the step of placing further comprises the method of affixing said indicium to skin of said patient (234).

Alternatively, the step of placing said indicium further comprises encircling said warning indicium around a portion of the patient (251). The portion of the patient (encircled at 251) is at least a portion of one of a torso, a limb, a neck, a head and extremities.

At step (260), the process is complete, and the apparatus is properly placed.

In another embodiment, the method further comprises providing a plurality of said indicia each with a separate respective warning against a respective prohibited physical treatment of a patient (242); positioning and placing said plurality of said indicia in a plurality of locations in a manner to preclude the respective physical access (243); and providing said separate respective warnings at locations on said respective plurality of said indicia to alert against physical access at said respective plurality of locations on said patient (252). The presence of said indicia significantly interferes with any reasonable application of the prohibited physical treatment on said patient.

In still another embodiment, the indicia provide a plurality of separate warnings against a respective plurality of prohibited physical treatments; and the indicia are placed such that said plurality of separate warnings at least in part inhibit access for each of said respective prohibited physical treatments for said patient. Prohibited physical treatments can be at least one of drawing blood, injections, pressure applications, physical contact and moisture application, or any other medical procedure or condition, measurement, withdrawal of body fluids, allergies, etc. (222).

An alternative to the method in steps 201 to 260 of FIG. 14, comprises providing a selected warning indicium to preclude a selected prohibited physical treatment of a patient (310), by affixing a warning indicium to the skin over a selected body part of the patient in such a way that subsequent to the placing, the warning on the indicium is visible and displays the warning to any person attempting the prohibited access of the body part to inhibit access to prevent the selected prohibited physical treatment (320). Thus with both illustrated embodiments, with the decal affixed to the skin or with the safety cover with the warning placed on an external outer surface of the physical barrier, the present invention provides a warning against the selected prohibited physical treatment, subsequent to the placing (330).

The actual graphic images used in accordance with the invention are not limited to the examples shown. Additionally, images (preferably that have been tested to be readily discernable by the medical profession) could supplement or replace the examples shown herein. Any image may be supplemented by textual warnings, and the warnings may appear in any number of languages.

In an alternate embodiment of the invention, the textual warnings stand-alone and are used in lieu of graphic images.

The warning indication graphic images can be one or more of graphics, icons, pictographs, and other visual, audible, or other method or means used to convey information regarding prohibited medical procedures to medical staff.

An alternate cover embodiment features glow-in-the-dark material on the warning, such that the warning would be visible in darkness or near darkness.

In all cover embodiments, the warning may be affixed to, woven into, painted or printed on, or otherwise made part of or visible from at least one surface of a safety sleeve or other barrier in accordance with the present invention. The key attribute of the warning is that once placed on the patient, it should provide a specific unambiguous warning indication, to clearly indicate to a health-care provider or medical staff, that specific medical procedures are to be prohibited on the protected body part.

In a preferred cover embodiment, more than one warning may be visible on the safety sleeve or other barrier embodiment. In this embodiment, each warning is a clear indication of a specific medical procedure that is prohibited for the protected body part. As a result, this embodiment of the invention simultaneously prohibits a plurality of different medical procedures.

In use, multiple instances of the warning indicium or other instructive indication embodiment may be used on one patient simultaneously, generally on different body parts. It is also possible to use multiple warning indicia on one specific body part.

The warning indicia can be made out of temporary dies, inks, powders, adhesive decals and any other disposable material that is durable enough to remain in place without easy removal, but non-toxic and flexible enough not to cause any discomfort or pain. The warning indicia should be removable by medical staff with a special solution specifically formulated for removal of the warning indicia or with commonly found materials such as alcohol, soap and water, etc. The materials can alternatively be chosen for solubility.

In a preferred embodiment, the materials selected for construction would permit easy sterilization of the invention prior to use.

In a preferred cover embodiment, the invention includes a means to detect if the invention has been tampered with and disregarded at any time during its use. This detection means may utilize any of single-use adhesive decals, color-change chemicals and phase-change chemicals. If the invention has been disregarded or attempted removal has taken place at any time, the detection means provides obvious and unchangeable evidence of such tampering.

In addition to tampering and removal, one embodiment of the present invention permits detection of unusual attributes such as elevated or depressed temperature, high or low pH values, presence or absence of moisture and so on. A different embodiment of the invention permits sensing of blood oxygenation level.

In an advanced cover embodiment, the safety sleeve includes motion and/or proximity sensors, using any conventional sensing means known to those skilled in the arts, including active and passive infrared (IR), ultrasonic, trembler, and vibration sensors. These sensors may trigger an alarm within some signalling range indicating attempted access or tampering with the warning indicium by someone external to the patient.

In a preferred cover embodiment, the material of the warning indicium is flexible, lightweight, inexpensive, sterile and disposable. In one cover embodiment, warning indicium may be one of water-resistant, water-proof or water-tight. In another embodiment, the warning indicium may be partly water-soluble or soluble only by a non-toxic chemical or compound other than water.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

What is claimed is:

1. A method to provide a specific warning in a manner to visually preclude a specific prohibited physical treatment of a patient, the method comprising:
   providing a visual warning of the prohibited physical treatement on a decal;
   placing the decal over a body part of the patient in such a way that subsequent to the placing, the warning on the decal is visible to display the warning to any person attempting the prohibited treatment of the body part.

2. The method as in claim 1, wherein said warning is specific to a medical condition and alerts against the prohibited physical treatment.

3. The method as in claim 1, wherein said warning additionally comprises at least one of a graphic image, a color warning, an icon warning and a textual warning.

4. The method as in claim 3, wherein said warning is a textual warning presented in a plurality of languages.

5. The method as in claim 1, further comprising providing a plurality of separate warnings on said decal.

6. The method as in claim 1, wherein the step of placing further comprises attaching said decal to cover a portion of clothing on said patient.

7. The method as in claim 1, wherein the step of placing further comprises affixing said decal to skin of said patient.

8. The method as in claim 1, wherein the step of placing said decal further comprises encircling said warning decal around a portion of the patient.

9. The method as in claim 8, wherein the portion of the patient is at least a portion of one of a torso, a limb, a neck, a head and extremities.

10. The method as in claim 1, further comprising:
    providing a plurality separate ones of said decals, each with a separate respective warning against a respective prohibited physical treatment of a patient; and
    placing said plurality of separate ones of said decals in a plurality of separate locations on the body of the patient in a manner to preclude the respective physical access to each of the separate locations to alert against physical access at said respective plurality of locations on said patient.

11. The method as in claim 1, wherein the presence of said decal significantly interferes with any reasonable application of the prohibited physical treatment on said patient.

12. The method as in claim 1, further comprising:
    providing said decal with a plurality of separate warnings against a respective plurality of separate prohibited physical treatments; and
    placing said decal carrying said plurality of separate warnings to at least in part inhibit access via said body part for each of said respective prohibited physical treatments for said patient.

13. The method as in claim 12, wherein said prohibited physical treatments are at least one of drawing blood, injections, pressure applications, physical contact and moisture application.

14. The method as in claim 1, wherein the decal is removable.

15. The method as in claim 1, wherein the decal is comprised of at least one of a temporary die, ink and paint.

16. The method as in claim 1, herein the decal is a single-use adhesive decal.

17. A method to provide a warning to preclude a prohibited physical treatment of a patient, the method comprising:
    affixing a warning decal to the skin over a body part of the patient so as to inhibit access to prevent the prohibited physical treatment; and
    positioning the decal in such a way that subsequent to the placing, the warning on the decal is visible to display the warning to any person attempting the access of the body part to provide a warning against the prohibited physical treatment.

18. The method as in claim 17, wherein said warning is specific to a medical condition and alerts against the prohibited physical treatment.

19. The method as in claim 17, wherein said warning additionally comprises at least one of a graphic image, a color warning, an icon warning and a textual warning.

20. The method as in claim 19, wherein said warning is a textual warning presented in a plurality of languages.

21. The method as in claim 17, further comprising the method of providing a plurality of separate warnings on said warning decal.

22. The method as in claim 17, wherein the step of placing said warning indicia further comprises the method of encircling said warning decal around a portion of the patient.

23. The method as in claim 22, wherein the portion of the patient is at least a portion of one of a torso, a limb, a neck, a head and extremities.

24. The method as in claim 17, further comprising:
    providing a plurality of separate ones of said warning decals each with a separate respective warning against a respective prohibited physical treatment of a patient; and
    positioning and placing said plurality of separate ones of said warning decals in a plurality of locations in a manner to alert against the respective physical treatment at said respective plurality of locations on said patient.

25. The method as in claim 24, wherein the presence of said warning decal significantly interferes with and precludes any reasonable application of the prohibited physical treatment on said patient.

26. The method as in claim 17, further comprising:
    providing said warning decal with a plurality of separate warnings against a respective plurality of separate prohibited physical treatments; and
    positioning and placing said warning decal carrying said plurality of separate warnings to at least in part inhibit access for each of said respective separate prohibited physical treatments for said patient.

27. The method as in claim 26, wherein said prohibited physical treatments are at least one of drawing blood, injections, pressure applications, physical contact and moisture application.

28. The method as in claim 17, wherein the decal is removable.

29. The method as in claim 17, wherein the decal is comprised of at least one of a temporary die, ink and paint.

30. The method as in claim 17, wherein the decal is a single-use adhesive decal.

31. A system for precluding a prohibited physical treatment of a patient, the system comprising:
   a decal, having a warning thereupon, affixable to the skin over a body part, of the patient to inhibit access to prevent the prohibited physical treatment;
   wherein the decal is positioned, placed and affixed, in such a way that subsequent to the placing, the warning on the decal is visible to display the warning to any person attempting the access of the body part.

32. The system as in claim 31, wherein said warning is specific to a medical condition and alerts against the prohibited physical treatment.

33. The system as in claim 31, wherein said warning additionally comprises at least one of a graphic image, a color warning, an icon warning and a textual warning.

34. The system as in claim 33, wherein said warning is a textual warning presented in a plurality of languages.

35. The system as in claim 31, wherein there are a plurality of separate warnings on said warning decal.

36. The system as in claim 31, wherein the decal is encircled around a portion of the patient.

37. The system as in claim 36, wherein the portion of the patient is at least a portion of one of a torso, a limb, a neck, a head and extremities.

38. The system as in claim 31, further comprising:
   a plurality of separate ones of said warning decals each with a separate respective warning against a respective separate prohibited physical treatment of a patient;
   wherein said plurality of separate ones of the warning decals are positioned in a plurality of locations in a manner to provide said separate respective warnings at said plurality of locations on said respective plurality of said separate ones of said warning decals in such a way that subsequent to the placing, the warning on the decal is visible to display the warning to any person attempting the access of the body part against the respective prohibited physical treatment.

39. The system as in claim 31, wherein the presence of said warning decal significantly interferes with any reasonable application of the prohibited physical treatment on said patient.

40. The system as in claim 31,
   wherein said warning decal provides a plurality of separate warnings against a respective plurality of prohibited physical treatments; and
   wherein the decal carrying said plurality of separate warnings is positioned in such a way that subsequent to the placing, the warning on the decal is visible to display the warning to any person attempting the access of the body part.

41. The system as in claim 40, wherein said prohibited physical treatments are at least one of drawing blood, injections, pressure applications, physical contact and moisture application.

42. The system as in claim 31, wherein the decal is removable.

43. The system as in claim 31, wherein the decal is comprised of at least one of a temporary die, ink and paint.

44. The system as in claim 31, wherein the decal is comprised of a single-use adhesive decal.

* * * * *